(12) United States Patent
Robertson (10) Patent No.: US 6,495,011 B2
(45) Date of Patent: Dec. 17, 2002

(54) APPARATUS FOR DETERMINATION OF ADDITIVES IN METAL PLATING BATHS

(75) Inventor: Peter M. Robertson, Winkel (CH)

(73) Assignee: Advanced Technology Materials, Inc., Danbury, CT (US)

(*) Notice: Subject to any disclaimer, the term of this patent is extended or adjusted under 35 U.S.C. 154(b) by 0 days.

(21) Appl. No.: 09/819,218

(22) Filed: Mar. 28, 2001

(65) Prior Publication Data

US 2001/0042694 A1 Nov. 22, 2001

Related U.S. Application Data

(62) Division of application No. 09/421,658, filed on Oct. 20, 1999, now Pat. No. 6,280,602.

(51) Int. Cl.⁷ .............................................. G01N 27/403
(52) U.S. Cl. ...................................... 204/434; 204/435
(58) Field of Search .......................................... 204/434

(56) References Cited

U.S. PATENT DOCUMENTS

| 4,479,852 A | 10/1984 | Bindra et al. |
| 5,192,403 A | 3/1993 | Chang et al. |
| 5,616,422 A | 4/1997 | Ballard et al. |
| 5,635,043 A | * 6/1997 | Tur yan et al. ............. 204/412 |

OTHER PUBLICATIONS

Freitag et al., "Analysis of Additives in Acid Copper Baths by Cyclic Voltammetry", Annu. Tech. Conf. Proc. Am. Electroplat. Soc., (1983), 70th, F–4, pp. 1–9.

* cited by examiner

Primary Examiner—T. Tung
Assistant Examiner—Alex Noguerola
(74) Attorney, Agent, or Firm—Margaret Chappuis; William Ryann (57) ABSTRACT

An apparatus and method for the indirect determination of concentrations of additives in metal plating electrolyte solutions, particularly organic additives in Cu-metalization baths for semiconductor manufacturing. The apparatus features a reference electrode housed in an electrically isolated chamber and continuously immersed in the base metal plating solution (without the additive to be measured). An additive concentration determination method comprises electroplating a test electrode at a constant or known current in a mixing chamber wherein the base metal plating solution is mixed with small volumes of the sample and various calibration solutions containing the additive to be measured. Plating potentials between the electrodes are measured and plotted for each of the solution mixtures, and data are extrapolated to determine the concentration of the additive in the sample. A multi-cycle method determines the concentration of both accelerator and suppressor organic additives in Cu plating solution in a single test suite.

7 Claims, 7 Drawing Sheets

APPARATUS FOR DETERMINATION OF ADDITIVES IN METAL PLATING BATHS

CROSS-REFERENCE TO RELATED APPLICATION

This is a division of U.S. patent application Ser. No. 09/421,658, filed Oct. 20, 1999, which is now U.S. Pat No. 6,280,602 in the name of Peter M. Robertson for "Method and Apparatus for Determination of Additives in Metal Plating Baths."

BACKGROUND OF THE INVENTION

1. Field of the Invention

The present invention generally relates to the determination of additives in metal plating baths, and more specifically to a method and apparatus for determination of organic suppressor and accelerator additives in semiconductor copper electrolysis plating baths.

2. Background of the Invention

Traditionally, aluminum (Al) has been used as the material of choice for metalization in forming interconnect layers in the manufacture of semiconductor microelectronic integrated circuits. Al is commonly deposited on semiconductor structures by chemical vapor deposition (CVD), which allows for precise control and highly uniform deposition of the product metal-containing film.

Despite the prior ubiquity of Al as a metalization medium, performance demands associated with increasing signal speeds and decreasing feature geometries of microelectronics have exceeded the capabilities of Al metal. Copper (Cu) therefore is increasingly being utilized as a semiconductor interconnect metal. The properties of Cu are not amenable to conventional CVD metalization approaches, due in part to the lack of suitable copper source reagents, and in consequence Cu is typically deposited on the microelectronic device structure via electroplating.

Electroplating of copper, however, has various associated problems.

Generally, Cu is plated onto a substrate by electrolysis in an etch solution, which may for example comprise copper sulfate, sulfuric acid, and hydrochloric acid. The plating process with an unaugmented etch solution of such type normally proceeds too rapidly. The result of such plating rapidity is that previously formed vias, i.e., passages to lower-level structures, e.g., electrodes or other conductors or semiconductor regions in the microelectronic device structure, are bridged over, and not filled with Cu. Accordingly, the desired electrical path to the underlying structure is not formed, and the semiconductor device structure must be reworked or discarded.

In order to combat such plating rapidity, the Cu plating process must be retarded. Additionally, the copper plating process requires acceleration in some aspects, to achieve desired coverage and leveling properties of the deposited metal. To achieve these concurrent opposing goals, organic additives are introduced into the copper electroplating bath to both slow down the plating process (suppressor additives) and to speed it up (accelerator additives). The speed of deposition of Cu on the substrate, and the quality and resulting electrical and mechanical properties of the metalization, are critically dependant on the concentration of these organic additives in the copper electroplating bath. However, the concentration of these additives is not constant, due to either "drag-out" by the wafers or by electrochemical reaction and loss during the electroplating. Accurate, real-time measurement of these electroplating bath additive concentrations, necessary for quality control, has been problematic.

The respective suppressor and accelerator organic compounds in the copper electroplating bath are usually present at very low, e.g., part-per-million by volume (ppmv) concentrations. This circumstance makes normal analytical procedures difficult to effectively apply, due to the masking effect of the high concentration of inorganic bath components (copper, acid, etc.). The most effective way of determining these organic compounds is by measuring their effect on the amount of Cu deposited.

Methods of measuring the effect of the concentration of the electroplating suppressors and accelerators are known in the art. U.S. Pat. No. 5,192,403, issued to Chang et al. on Mar. 9, 1993, describes one such method, comprising the steps of:

a) preparing a basis solution which contains all of the components of the plating solution to be measured (the "sample"), except the component of interest;

b) preparing a calibration solution which contains the component of interest in a known concentration near that which would be expected in the sample;

c) adding measured amounts of the calibration solution to a first defined volume of the basis solution, and plotting the copper plating (cathodic) charge in cyclic voltammetry in the mixed solution against the added volume of the calibration solution;

d) adding measured amounts of the sample solution to a second volume of the basis solution, and plotting the copper plating (cathodic) charge in cyclic voltammetry in the mixed solution against the added volume of the sample; and e) comparing the slopes of the calibration standard curve and the sample mixture curve to determine the concentration of the component of interest in the sample solution.

Variations of this technique are employed in the art to measure the concentrations of organic suppressor and accelerator additives in Cu electroplating baths for semiconductor manufacturing. These techniques variously measure the plating charge or stripping (de-plating) charge, e.g., for electro-plate deposition of Cu directly onto a test electrode via current supplied to a counting electrode in a plating step, and removal of previously plated copper in a stripping step. The charge is generally obtained by measuring the plating or stripping current while holding the voltage constant, and integrating to obtain the charge. Typically, an electrode is cyclically plated and de-plated (stripped of the previously deposited Cu) multiple times for each quantity measured. Each plating/measurement cycle comprises the following steps:

Clean—the test electrode surface is thoroughly cleaned electrochemically or chemically using acid bath, followed by flushing with water or acid bath, Equilibrate (optional)—the test electrode and a reference electrode are exposed to the plating electrolyte and allowed to reach an equilibrium state.

Plate—Cu is electroplated onto the test electrode either at constant potential or during a potential sweep and the current between the test and counter electrodes is monitored and recorded, and Strip—the Cu deposition is removed (e.g., by reversal of the plating current flow and/or exposure to an acid bath) by suitably changing the potential between the test and counter electrodes stepwise or in a sweep in the reverse direction and the current between the test and the counter electrode is monitored and recorded (and integrated to determine the "stripping charge").

These four steps must be repeated for each plating/measurement cycle; each sample measurement is typically repeated several times to eliminate random errors introduced by variations in process conditions, e.g., composition, temperature, etc. Hence, an entire concentration determination sequence can require a considerable period of time to complete. To be useful as a quality control tool in copper metalization in semiconductor manufacturing, the concentration determination must be completed in a very short time frame so that significant depletion of the organic additives in the plating bath does not occur. Any significant depletion of organic additives during the determination will render the analytical method useless.

It would therefore be a significant advance in the art, and is accordingly an object of the present invention, to significantly reduce the time required for the concentration determination sequence to be completed, relative to the present state of the art.

To allow for fine control of the plating process, it is also desirable that concentration of organic additives be determined to a high degree of accuracy. Is therefore is a further objective of the present invention to determine the organic additive concentrations to a high degree of precision, preferably less than 10 percent of indicated value, and more preferably less than about five percent of indicated value.

It is another object of the invention to provide an improved system for determination of organic additive concentration in a copper electroplating bath, that is simple in operation, economic in capital cost and operating expense, and efficient in characterization of the electroplating medium.

Other objects and advantages will be more fully apparent from the ensuing disclosure and appended claims.

SUMMARY OF THE INVENTION

The present invention relates in one aspect to an apparatus for the determination of concentrations of organic additives in a Cu electroplating bath, comprising
- a reference electrode, housed in an electrically isolated reference chamber and immersed in a base metal plating solution;
- a test electrode having a plating surface upon which metal is depositable by electroplating, disposed in a measurement chamber containing an electroplating current source electrode, wherein metal plating solutions containing unknown concentrations of additives are introduced to, and intermixed with, the base metal plating solution;
- a capillary tube joining the reference chamber and the mixing chamber in unidirectional fluid flow relationship, whereby base metal plating solution is transferred to the measurement chamber from the reference chamber, and wherein the measurement chamber end of the capillary tube is disposed in close spatial relationship to the plating surface of the test electrode;
- selectively controllable electroplate driving electronics electrically and operatively coupled between the test electrode and the electroplating current source electrode, whereby metal is selectively deposited onto the test electrode from the mixed metal plating solution in the mixing chamber at a constant or known current density; and
- electrical potential measuring circuitry electrically and operatively coupled between the test electrode and the reference electrode, whereby electrical potential between the electrodes is measured and recorded.

The present invention relates in another aspect to a method for measuring the characteristic decisive potential of a mixed metal plating solution by performing a plating/measuring cycle, comprising:
- cleaning the test electrode and measuring chamber by a method selected from the group consisting of acid bath exposure, electrolytic cleaning with or without gas (oxygen) generation and water flush, and combinations thereof;
- flowing a first known volume of base metal plating solution without the component of interest from the reference chamber through the capillary tube into the measurement chamber;
- optionally adding to the measuring chamber a second known volume of metal plating solution containing some concentration of the component of interest and mixing the solutions;
- allowing the test electrode to come to an equilibrium state in the mixed metal plating solution, such that there exists no electrical potential between the reference electrode and the test electrode;
- depositing metal onto the test electrode from the mixed metal plating solution in the mixing chamber by electroplating at a constant or known current density;
- measuring and recording the decisive electrical potential between the reference electrode and the test electrode at a set time after initiation of the plating step, whereby sufficient stability has been reached;
- measuring and recording the equilibrium electrical potential between the reference electrode and the test electrode following completion of the plating step, whereby the current flow in the electroplating circuit is zero;
- calculating the over-potential by subtracting the equilibrium potential from the decisive potential;
- stripping the deposited metal from the test electrode by a method selected from the group consisting of chemical stripping, application of reverse bias electroplating current, and combinations thereof.

The present invention relates in another aspect to a method for conditioning the base plating solution for the determination of organic additives in metal plating solutions, comprising:
- adding to the first known volume of base metal plating solution in the measuring vessel a known volume of additive and performing plating and stripping operations, whereby the non-linearity of the response of the decisive potential to the additive is "masked," and all decisive potential measurements are carried out in the linear region of the response, this optional conditioning of the base metal plating solution being performed prior to the introduction of the sample to be determined.

The present invention relates in another aspect to an algorithm for determination of the concentration of organic additives in metal plating solutions, comprising:
- plotting values calculated as the inverse of the ratio of the measured potential of each metal plating bath solution containing additives to the measured potential of the metal plating bath solution containing the sample, minus one;
- linearly extrapolating back through these points to determine the point corresponding to the value of the inverse of the expression:

[(the measured potential of metal plating for that solution, with no additives)/(the measured potential of metal plating for that solution, containing the sample)]−1; and calculating the negative inverse of the value.

The present invention is based in part on applicant's discovery of a technique to dramatically reduce equilibration time of the reference electrode in an apparatus for the determination of concentration of additives by the Pulsed Cyclic Galvanostatic Analysis (PCGA) technique. In conventional practice, a reference electrode is disposed in the same electrolyte solution as is the test electrode upon which Cu is deposited. Following each plating/measurement cycle, the test electrode must be stripped of the deposited Cu, and cleaned to remove all traces of the test solution (which contains some level of additive). The test electrode and the reference electrode are then re-immersed in the base copper plating electrolyte solution, and must return to an equilibrium state prior to initiation of the next plating/measurement operation.

In one embodiment of the present invention, the reference electrode resides in a reference chamber that is physically and electrically isolated from the mixing chamber that houses the test electrode (upon which Cu is deposited). The reference electrode is continuously immersed in the base copper plating electrolyte solution. By never exposing it to the variously doped bath solutions in the mixing chamber, the reference electrode need not be cleaned following each plating/measurement cycle. Thus, it remains continuously "equilibrated" to the base copper plating electrolyte solution, and the equilibration step is reduced to the time necessary for the test electrode to "equilibrate" to a fresh base copper plating electrolyte solution. This reduces the equilibration step by roughly an order of magnitude over the prior art, i.e., to approximately two minutes.

The reference chamber is connected in fluid flow relationship to the mixing chamber by a capillary tube, whose mixing chamber terminal end is in close physical proximity to the plating surface of the test electrode. By this arrangement, the apparatus of the present invention achieves several additional advantages, including:

Potential difference (iR drop) across the electrolyte is eliminated or dramatically reduced.

The measuring chamber is filled with base copper plating electrolyte solution for each cycle through the capillary tube, from the reference chamber. Both electrodes are hence initially immersed in the same electrolyte.

The flow of base copper plating electrolyte solution through the capillary tube and against the plating surface of the test electrode facilitates the removal of air on the test electrode, contributing to consistent cycle-to-cycle measurements.

The flow of base copper plating electrolyte solution through the capillary tube generates a fresh and reproducible liquid junction to the measuring vessel.

Additional aspects, features and embodiments of the invention will be more fully apparent from the ensuing disclosure and appended claims.

DETAILED DESCRIPTION OF THE INVENTION, AND PREFERRED EMBODIMENTS THEREOF

The apparatus of the present invention utilizes a reference electrode housed in a reference chamber and continuously immersed in a base copper plating electrolyte solution; a test electrode upon which Cu is deposited and removed in each plating/measurement cycle, disposed within a measurement chamber wherein various solutions containing additives are introduced to the base copper plating electrolyte solution; a capillary tube joining the reference chamber and the mixing chamber in unidirectional fluid flow relationship, for introducing fresh base copper plating electrolyte solution into the measurement chamber for each plating/measurement cycle, wherein the measurement chamber end of the capillary tube is disposed in close physical proximity to the plating surface of the test electrode; and driving electronics operationally coupled to the test and plating current source electrodes and measurement electronics operationally coupled to the reference electrode and the test electrode.

Figure 1:
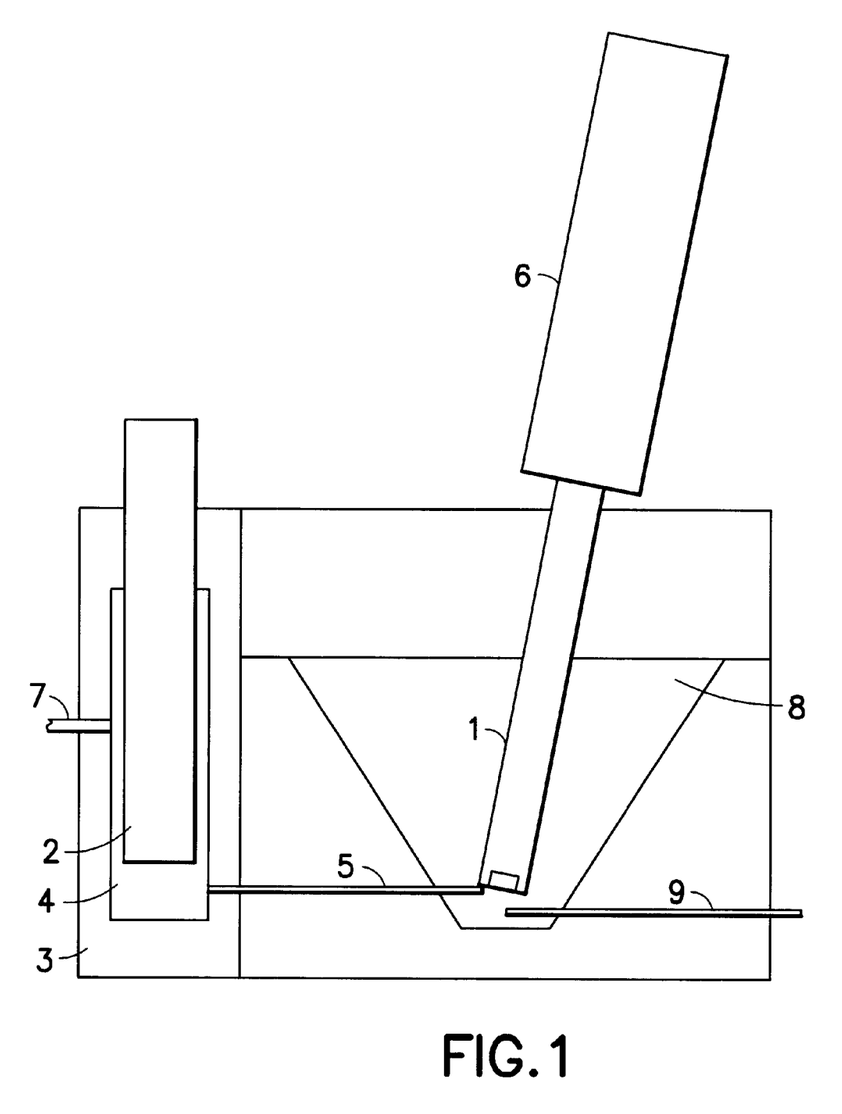
FIG. 1 is a schematic representation of a system of the present invention according to one embodiment thereof.

Referring to FIG. 1, reference electrode 2 is disposed in reference chamber 3, and continuously immersed in base copper plating electrolyte solution 4. Base solution 4 is injected into reference chamber 3 through fluid flow inlet 7, and flows into measuring chamber 8 via capillary tube 5. Additional solutions containing additives (sample solution and calibration solution(s)) are introduced into the measuring chamber (through means not depicted in FIG. 1) and thereby mixed with the base copper plating electrolyte solution introduced therein through capillary tube 5. Fluid pressure differential, and/or fluid flow valves prevent the propagation of mixed electrolyte solution from measuring chamber 8 to reference chamber 3. Thus, reference electrode 2 is continuously, exclusively immersed in base copper plating electrolyte solution 4.

The measuring chamber end of capillary tube 5 is disposed in close proximity to the plating surface of test electrode 1, preferably within a few mm. This close spatial relationship prevents air bubble formation on the plating surface of test electrode 1, and reduces or eliminates the effect of potential difference (iR drop) in the electrolyte. Plating current source electrode 9 is electrically and operatively coupled to test electrode 1 through a suitable, reversible, controllable current source (not shown). Test electrode 1 is preferably comprised of a platinum or glassy carbon (vitreous carbon) substrate, although it is not restricted to these materials. Test electrode 1 is preferably mechanically and electrically coupled to rotational driver 6, or driver 6 and electrode 1 may be combined in a unitary rotating disc electrode, as is known in the art. Use of a rotating disk electrode increases the accuracy and consistency of measurements across cycles by stirring the electrolyte solution contained in the measurement chamber.

Alternatively, test electrode 1 may be an ultra-micro electrode with diameter less than 50 microns and preferably less than 10 microns where forced agitation of the electrolyte mixture within measurement chamber 8 is not necessarily required. As a still further alternative, a small-scale mixer, ultrasonic vibrator, mechanical vibrator, propeller, pressure differential fluid pump, static mixer, gas sparger, magnetic stirrer, fluid ejector, or fluid eductor may be deployed in the measurement chamber 8, to effect hydrodynamic movement of the fluid with respect to the test electrode. In all embodiments, test electrode 1 is preferably tilted at an angle from vertical, to prevent the collection and retention of air bubbles on its surface. Suitable means (not shown in FIG. 1) for measuring electrical potential between the test electrode and the reference electrode are employed.

Suitable means for electrolyte solution following completion of each cycle, while not shown in FIG. 1, are employed. Additionally, acid bath and rinsing water may be injected into and drained from measurement introducing electrolyte solutions containing additives (sample or calibration solutions) into measurement chamber 8, as well as suitable means for purging measurement chamber 8 of chamber 8, and a forced fluid purging means may optionally be provided. These ancillary functions are easily provided by means well known in the art, and are not shown in FIG. 1 or discussed at length in the present disclosure.

Figure 2:
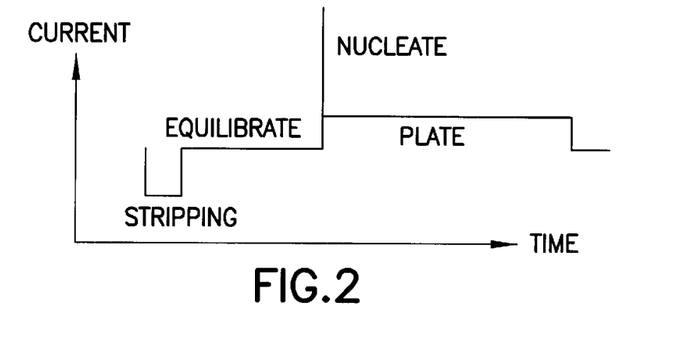
FIG. 2 is a graph depicting the four steps of a PCGA cycle.

The organic additive concentration determination method of the present invention is an adapted methodology of Pulsed Cyclic Galvanostatic Analysis (PCGA). PCGA is utilized in connection with the apparatus of the present invention to perform multiple plating/measurement cycles in mixed electrolyte solutions containing various known and unknown concentrations of additives. In each plating/measurement cycle, the test electrode and measuring chamber are first thoroughly cleaned, e.g., electrolytically in an acid bath followed by a water and/or forced air flush. Base electrolyte solution is then introduced into the measuring chamber from the reference chamber, mixed with other electrolytes (containing additives), and the test electrode allowed to equilibrate. Cu is then deposited onto a plating surface on the test electrode by electroplating in the mixed electrolyte solution, at a known or constant current density. The deposited Cu is then stripped from the test electrode by reverse biasing the electroplating circuit and/or by chemical stripping. Measurements of electrical potential between the test and reference electrodes are recorded throughout the cycle. The four basic steps of each cycle—Clean, Equilibrate, Plate, and Strip—and the associated measured potentials are depicted in the graph of FIG. 2.

A single plating/measurement cycle of the PCGA technique performed with the apparatus of the present invention comprises the following steps:

1) The test electrode and measurement chamber are cleaned by an acid wash followed by a water flush and/or a forced air purge.
2) Fresh base copper plating electrolyte solution is introduced to the measurement chamber from the reference chamber through the capillary tube.
3) Solutions of copper plating electrolyte variously "doped" with organic additives (according to the methodology of the present invention) are introduced to, and intermixed with, the base copper plating electrolyte solution in the measurement chamber.
4) Following equilibration of the test electrode, Cu is deposited via electroplating onto the test electrode at a known or constant current density for a set time sufficient to ensure stability, and the electrical potential between the test electrode and the reference electrode is measured and recorded (the "decisive potential"). A significant feature of the apparatus and method of the present invention is that the reference electrode, being continuously exclusively immersed in fresh base copper plating electrolyte solution, requires no equilibration, hence significantly reducing the overall cycle time.
5) Following the plating step, with zero current flow in the electroplating circuit, the electrical potential between the test electrode and reference electrode is again measured and recorded (the "equilibrium potential"). The over-potential is determined by subtracting equilibrium potential from the decisive potential.
6) The deposited Cu is stripped from the test electrode by reversed biasing the plating circuit, and/or the introduction of chemical stripping agents into the measurement chamber. The electrical potential between the test electrode and reference electrode is again measured and recorded (the "stripping potential").

Concentrations of organic additives in copper plating electrolyte baths are calculated indirectly, according to the multiple-plating/measurement cycle technique of Pulsed Cyclic Galvanostatic Analysis (PCGA). In general, PCGA comprises the following steps, wherein each step calling for a plating/measuring cycle is actually performed multiple times (e.g., four times) and the results averaged, to eliminate random errors:

1) preparing a base copper plating electrolyte solution ("basis solution") which contains all of the components of the plating solution to be measured (the "sample"), except the component of interest;
2) preparing a plurality of calibration solutions each of which contains the component of interest in a known concentration ("standard addition") in excess of that which would be expected in the sample;
3) performing a plating/measuring cycle in the basis solution and optionally adding a known volume of additive (suppressor) in order to eliminate non-linear response behavior, and measuring the electrical potential between the test electrode and reference electrode at a set time after beginning the plating phase (the "decisive potential"), and again following the plating step, with zero current flow in the electroplating circuit (the "equilibrium potential), and calculating the over-potential by subtracting equilibrium potential from the decisive potential.
4) adding a measured amount of the sample solution to a known volume of the basis solution, performing a plating/measuring cycle in the mixed solution, and measuring the decisive potential and the over-potential of the mixed solution.
5) adding a measured amount of the first calibration solution (containing the first standard addition) to the same volume of fresh basis solution, performing a plating/measuring cycle in the mixed solution, and measuring the decisive potential and the over-potential of the mixed solution;
6) repeating step 5 for each calibration solution, containing each standard addition; and
7) plotting the reciprocals of the decisive potentials and/or the over-potentials measured on a reciprocal concentration scale, and performing a linear extrapolation back to the basis measurement to obtain the negative reciprocal of the sample concentration of the component of interest.

As an aid to a more complete understanding of the invention, a formulistic representation of the data transformation and plotting method of step 7 above is set out below:

| Notation: | m1 | basis measurement |
| | m2 | sample measurement |
| | m3 | first standard addition measurement |
| | m4 | second standard addition measurement |
| Transformation: | | |
| response | | concentration |
| m3' = 1/(m3/m2 − 1) | | 1/standard addition one |
| m4' = 1/(m4/m2 − 1) | | 1/standard addition two |
| m1' = 1/(m1/m2 − 1) | | −1/sample |

The data points at m3' and m4' are linearly extrapolated back to m1' and the negative reciprocal sample concentration is thereby obtained.

The said method of data treatment can, however, be replaced by a more conventional one such as a polynomial curve fitting of the response as a function of the volume of additive added with an extrapolation back to zero response, which give the negative additive concentration in the sample.

Some additives, which give high instrumental response at very low concentrations and level off to a limiting response at high concentration, are difficult to determine at high concentration in the absence of a theoretical or empirical description of the non-linearity of response. Because of the initially large response at very low concentration and much less sensitivity at high concentration, standard addition methods of calibration and simple polynomial fitting can fail to give the correct extrapolation. However, if an addition of the active substance is done before any background or sample determination is performed the response curve is shifted to the linear and less sensitive region, which allows an easier determination to be made with much lower extrapolation error.

This method is particularly applicable for the determination of surface active compounds used in metal plating processes—in particular the so-called "suppressors" or "carriers" used in electroplating of metals. These substances have a great effect on the electro-deposition at very low concentrations because of the great affinity to form a monolayer at the electrode interface.

Figure 3:
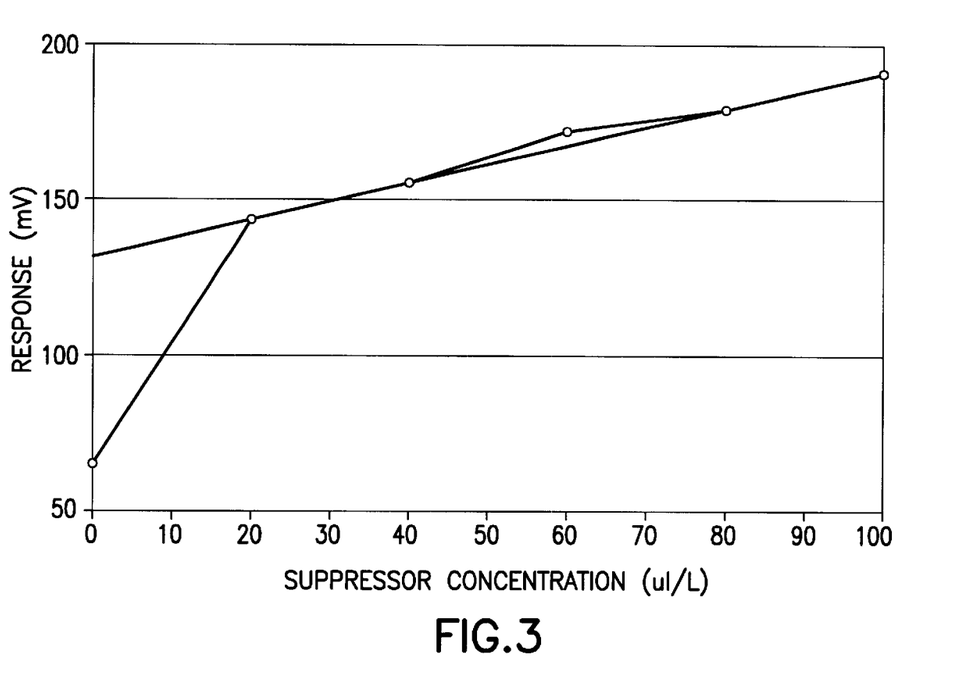
FIG. 3 is a graph depicting the non-linear and linear areas of the response curve for some types of additives.
Figure 4:
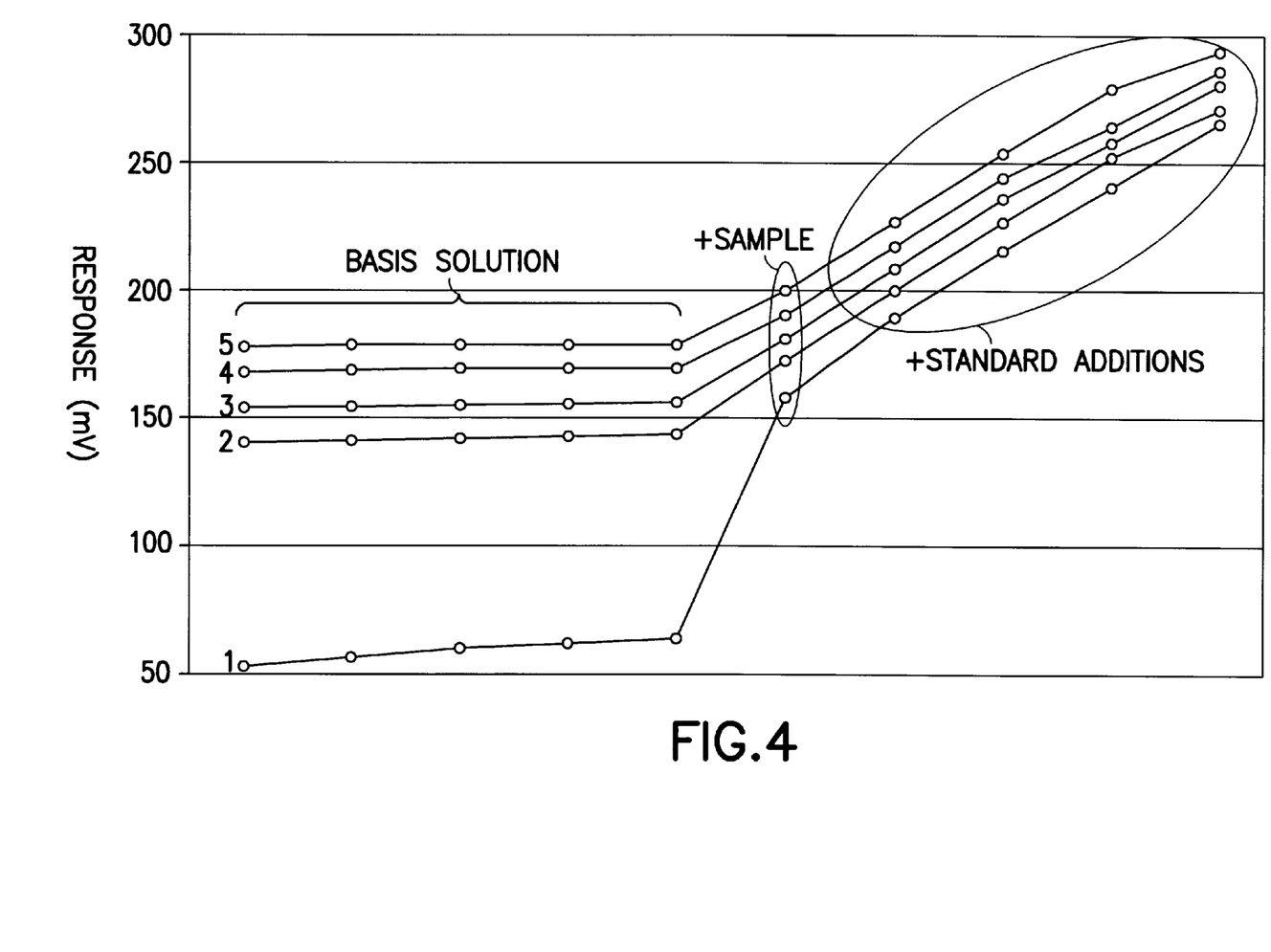
FIG. 4 is a graph depicting the non-linear and linear response curves of various concentrations of certain additive measurements.

An example of such a system and its response is depicted in graph of FIG. 3. At suppressor concentrations below 20 uL/L a very large change of response is observed, and above this concentration the response is almost linear (with "tailing-off" into a plateau region). Although the response in the "linear" region at concentrations above 20 uL/L shows a lower sensitivity to the suppressor concentration, this is desirable since typical plating bath compositions have the suppressor at extremely high concentration (25 mL/L). Hence, in the broad practice of the present invention to determine the concentrations of such additives, the initial "background" measurement may not be performed in a base metal plating electrolyte solution totally lacking the additive, but instead may be performed in a metal plating electrolyte solution containing a sufficient added concentration of the additive to generate a measured response in the linear region of the response curve. Successive measurements would then be performed in metal plating electrolyte solutions to which the sample or additional standard additions (calibration amounts) of additive were introduced in addition to the initial additive amount. The graph of FIG. 4 shows a comparison of some determinations without suppressor conditioned basis (background) solution (curve 1) and with suppressor conditioned basis solutions at concentrations of 20, 40, 60, and 80 uL/L (curves 2 through 5, respectively).

In one embodiment of the present invention, the concentrations of both accelerator and suppressor organic additives in copper-metal semiconductor plating electrolyte baths are determined in a single PCGA analysis, as follows (wherein each step calling for a plating/measuring cycle is actually performed multiple times (e.g., four times) and the results averaged, to eliminate random errors):

1) Perform a plating/measuring cycle in a base copper plating electrolyte solution ("basis solution") which contains all of the components of the plating solution to be measured (the "sample"), with the exception of accelerator and suppressor organic additives. This is the background measurement for the suppressor additive concentration determination. Optionally and ideally the background measurement is made in the presence of a known volume addition of the additive (suppressor) whereby this measurement and all following decisive potentials measured are in a linear section of the response curve.

2) Add a small amount of sample (preferably less than 1 ml and greater than 0.01 ml and most preferably about 0.1 ml) to a known fixed volume (the "standard volume" which is less than 100 ml and preferably 10 ml) of basis solution, and perform a plating/measuring cycle in the mixed solution.

3) Add a first standard addition of suppressor additive to a standard volume of fresh basis solution, and perform a plating/measuring cycle in the mixed solution.

4) Repeat step 3 using at least a second standard addition of suppressor additive, and optionally a third, fourth, etc., standard addition.

5) Add an excess of suppressor additive to a standard volume of fresh basis solution, and perform a plating/measuring cycle in the mixed solution. This is the background measurement for the accelerator additive concentration determination.

6) Add a larger amount of sample to a standard volume of basis solution containing the excess of suppressor additive as in step 5. A greater amount of sample is required than was required for step 2, because of the generally lower sensitivity of the plating process to the accelerator additive than the suppressor additive. Perform a plating/measuring cycle in the mixed solution.

The volumes of additives that must be employed are dependent on the concentrations set by the bath manufacturer and must therefore be adjusted accordingly, as may be performed without undue experimentation by those of ordinary skill in the art.

7) Add a first standard addition of accelerator additive to a standard volume of basis solution containing the excess of suppressor additive as in step 5, and perform a plating/measuring cycle in the mixed solution.

8) Repeat step 7 using at least a second standard addition of accelerator additive and optionally a third, fourth, etc., standard addition.

9) Analyze the measured data for the suppressor and accelerator additives separately, according to the methodology described hereinabove, to determine the suppressor and accelerator additive concentrations in the sample.

Figure 5:
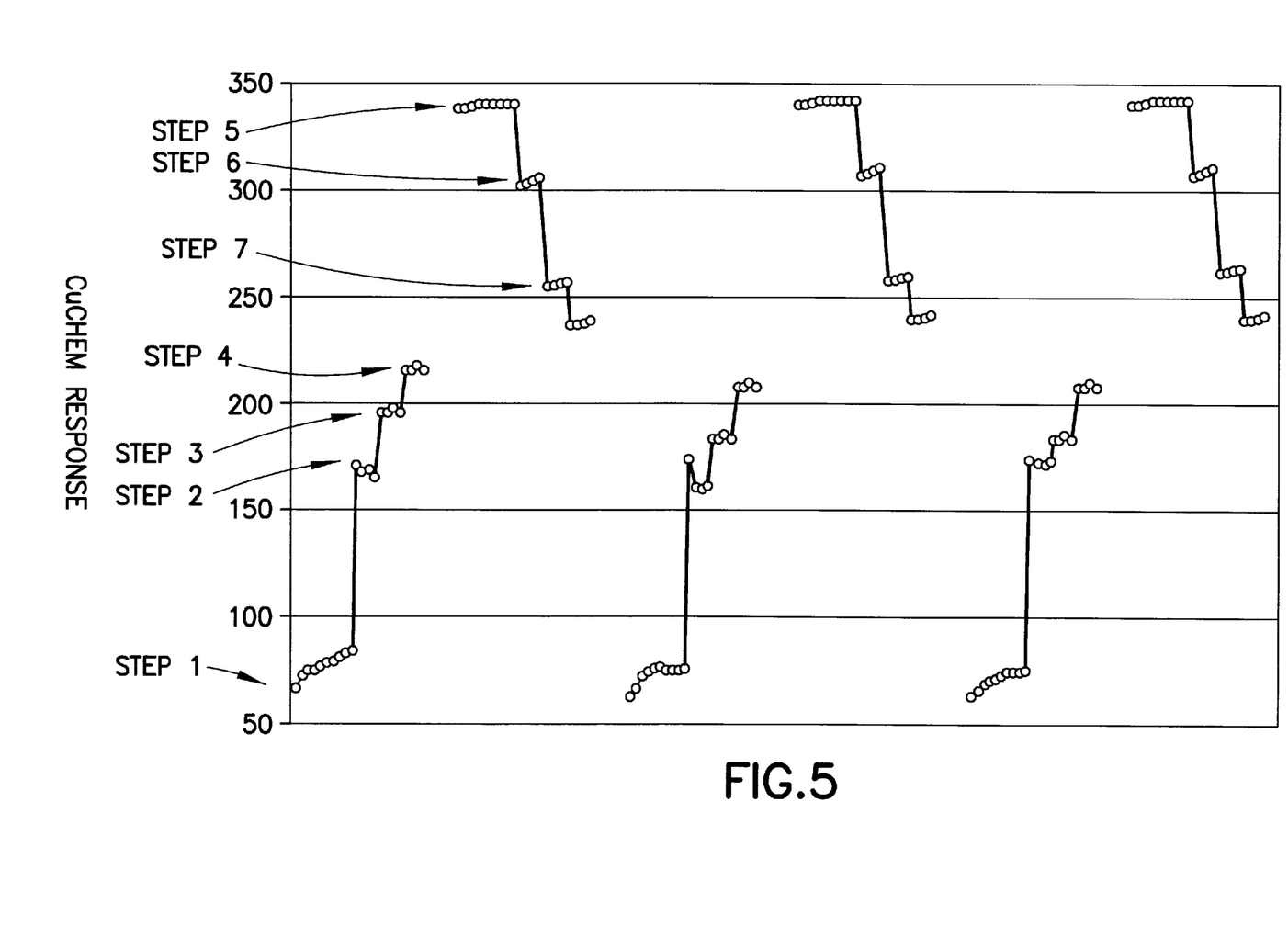
FIG. 5 is a graph depicting a suppressor/accelerator concentration determination according to one embodiment of the present invention.

The graph of FIG. 5 is representative of the data obtained from a suppressor/accelerator concentration determination according to this process, wherein the data are labeled to correspond to the above-described steps.

The invention will be further understood and illustrated by the following non-limiting example.

EXAMPLE

In addition to the measuring vessel described above, the analyzer consists of 4 digital burettes that are filled with the following solutions:

| | |
|---|---|
| Burette 1 | the sample itself collected from an overflow sample capture vessel |
| Burette 2 | diluted (25 x) accelerator additive |
| Burette 3 | diluted (25 x) suppressor |
| Burette 4 | the base solution composed of 70 g/l cupric sulfate pentahydrate 180 g/l 95–97% sulfuric acid 60 ppm chloride as hydrochloric acid |

The analyzer was programmed to perform the following sequence. The overall operation given in terms of the actual command code used on the analyzer was as follows:

| 1 | 2 | 3 | 4 | 5 | 6 | 7 | 8 | 9 | 10 | 11 |
|---|---|---|---|---|---|---|---|---|---|---|
| C3 | S20 | C3 | FIL | Bsp | INs | SUP | C3 | Bac | INa | ACC |
| 0.1 | 0.1 | 0.04 | 4 10.0 | | 0.4 | 3 | 2.0 | | 6.0 | 2 |

This sequence of commands has the following significance:

| | | |
|---|---|---|
| 1 | C3 | a pre-analysis step to prime the dispensing tip of burette 3 by dispensing 0.1 ml |
| 2 | S20 | a sampling operation in which burette 1 is filled with fresh sample and the dispensing tube (using flow segregation) with 1 ml of a 20 x diluted sample |
| 3 | C3 | the background level for the suppressor determination is raised by adding 0.04 ml of diluted suppressor from burette 3 |
| 4 | FIL | the measurement vessel is filled with 10 ml of the basis solution from burette 4 |
| 5 | Bsp | the background measurement for the suppressor is carried out. This command performs the clean, equilibrate, plate and strip operations |
| 6 | INs | 0.4 ml of diluted sample is added |
| 7 | SUP | the suppressor measurement is carried out using the standard addition procedure and repeated clean, equilibrate, plate and strip operations. Burette 3 is used for the standard additions of diluted suppressor |
| 8 | C3 | an excess of suppressor (2 ml) is added to prepare for the accelerator determination |
| 9 | Bac | the background measurement for the accelerator is carried out. This command performs the clean, equilibrate, plate and strip operations |
| 10 | INa | 6.0 ml of the sample is added - the remaining diluted sample is injected first followed by the pure sample. The injection volume is automatically corrected (increased) by the appropriate amount to account for the part injection of diluted sample. |
| 11 | ACC | the accelerator is measured with standard addition procedure and repeated clean, equilibrate, plate and strip operations. Burette 3 is used for the standard additions of diluted suppressor |

The clean, equilibrate, plate, strip cycle used for the suppressor background measurement (Bck) the accelerator background measurement (Bac) and the suppressor and accelerator measurements themselves (SUP), (ACC) is as follows:

| | |
|---|---|
| Clean | the test electrode is polarized anodically with a current of 2 mA for 10 seconds |
| Equilibrate | the test electrode is left to equilibrate at zero current for 20 seconds |
| Plate | the test electrode is polarized cathodically at 1 mA for 10 seconds |
| Strip | (optional) the test electrode is polarized anodically with a current of 1 mA for 1 second |

Figure 6:
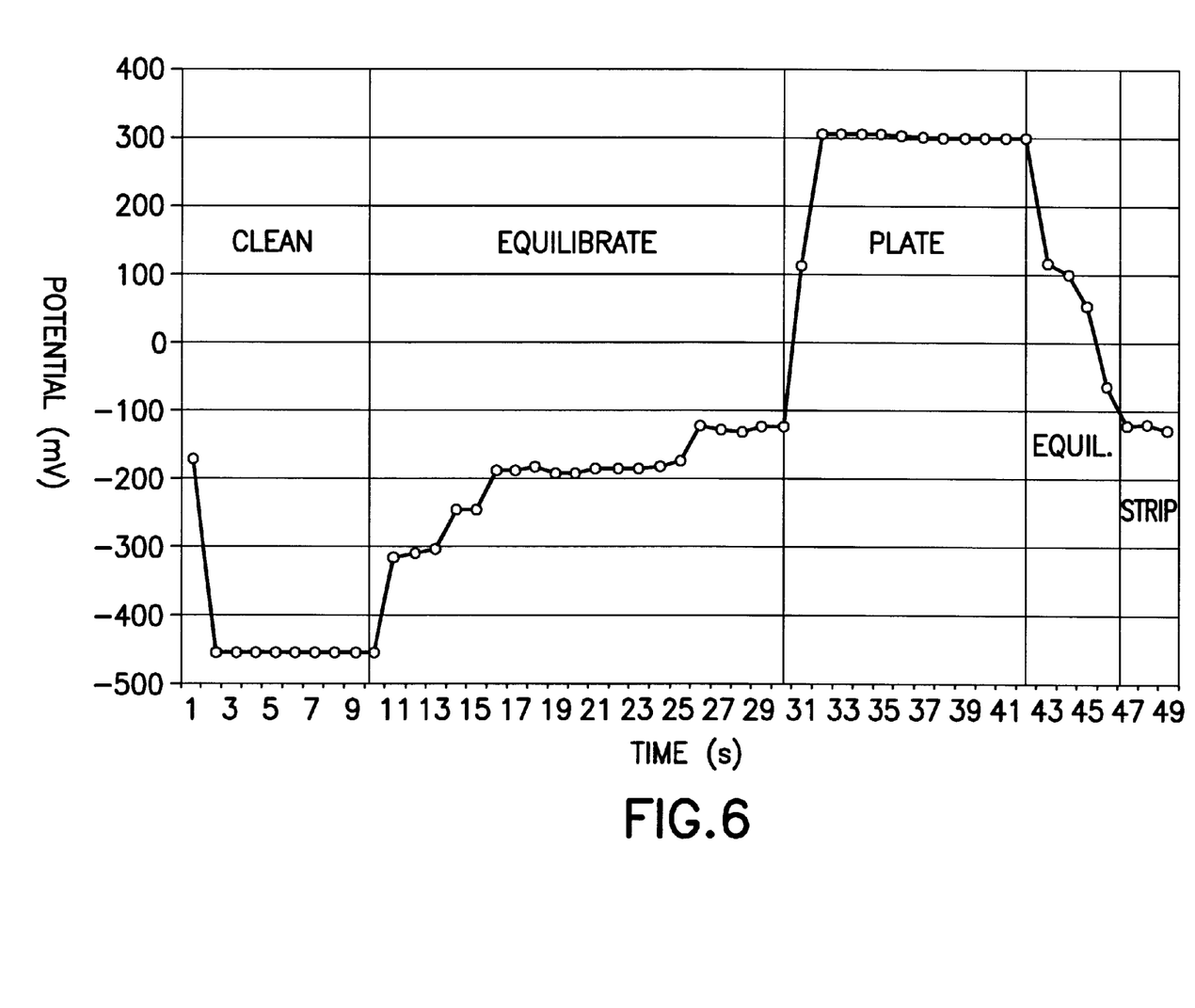
FIG. 6 shows the response curve during the clean, equilibrate, plate and strip cycles according to one embodiment of the present invention.

FIG. 6 shows the response curve during the clean, equilibrate, plate and strip cycles. The potential is measured at the reference electrode with the test electrode grounded.

Figure 7:
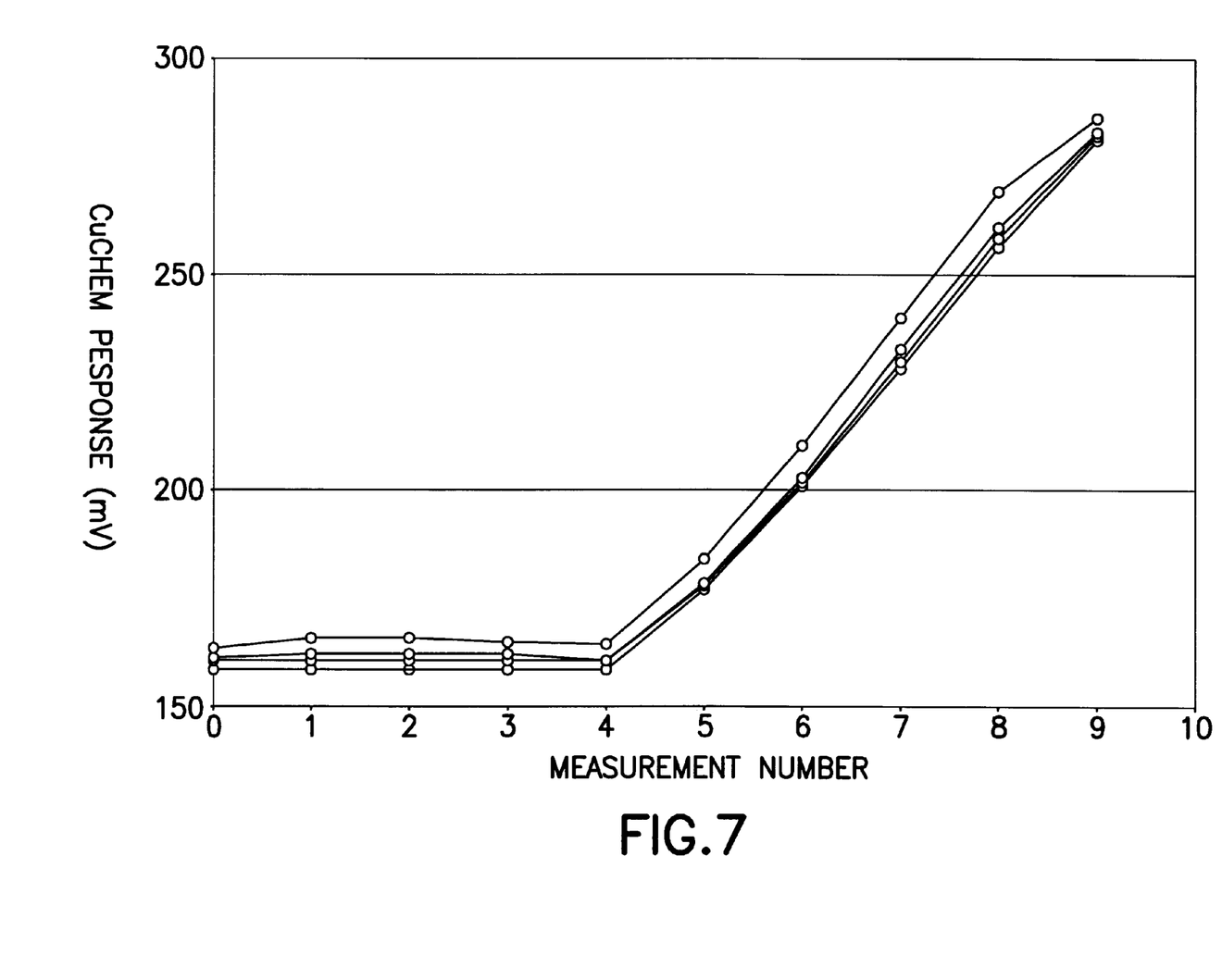
FIG. 7 shows the response for the suppressor additive measurement according to one embodiment of the present invention.

FIG. 7 shows the response for the suppressor additive measurement.

Figure 8:
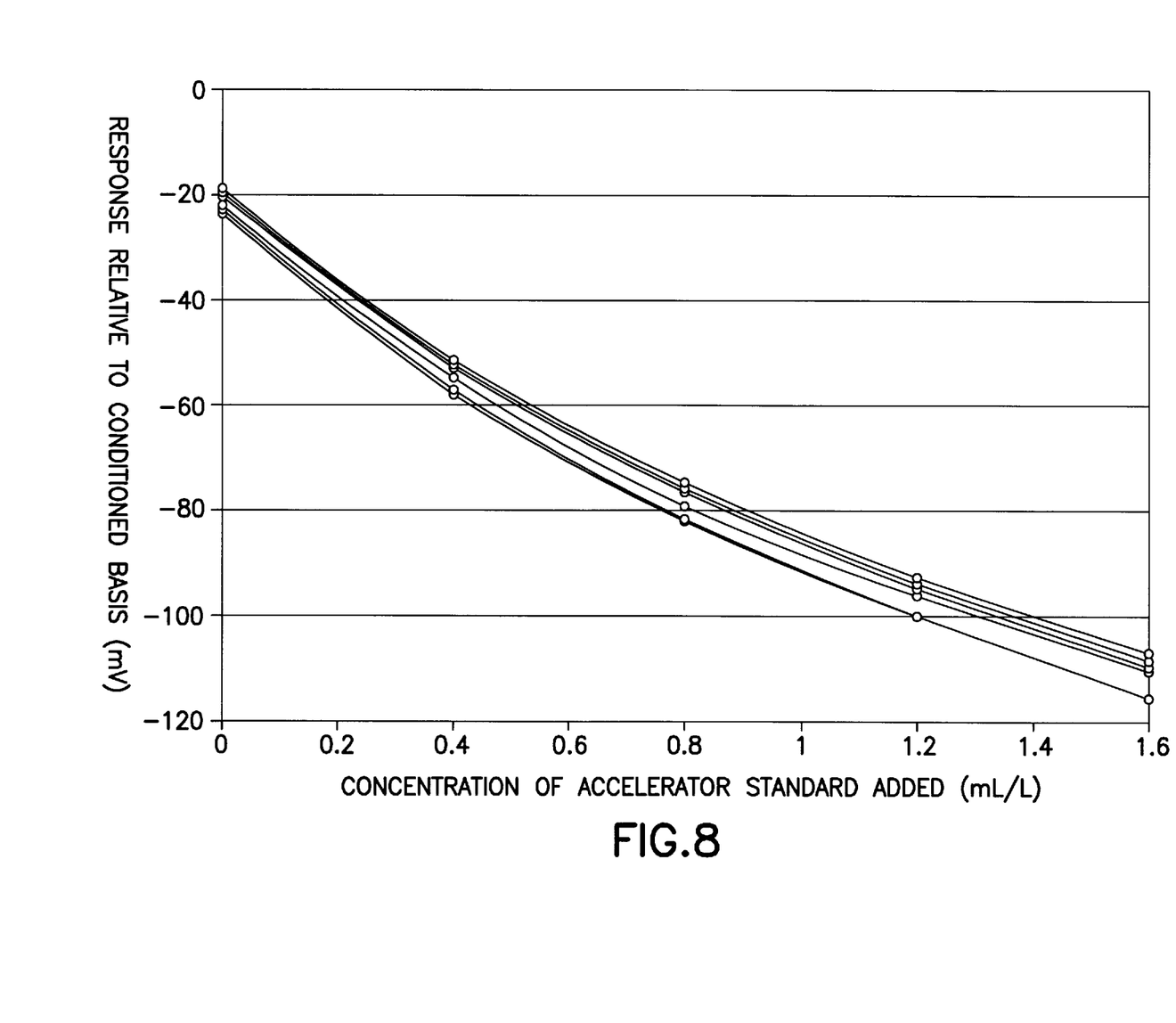
FIG. 8 shows the response for the accelerator additive measurement according to one embodiment of the present invention.

FIG. 8 shows the response to the accelerator additive measurement.

Typically the results obtained from these measurements were:

Suppressor 26.4 ml/l

Accelerator 1.05 ml/l

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. An apparatus for determining the concentration of additives in a metal plating bath, comprising:

a reference electrode, housed in an electrically isolated reference chamber and immersed in a base metal plating solution;

a test electrode having a plating surface upon which metal is depositable by electroplating disposed in a measurement chamber containing an electroplating current source electrode, wherein metal plating solutions containing known and unknown concentrations of additives are introduced to, and intermixed with, the base metal plating solution;

a capillary tube joining the reference chamber and the mixing chamber in unidirectional fluid flow relationship, having a reference chamber end disposed in the reference chamber and a mixing chamber end disposed in the mixing chamber, whereby base metal plating solution is transferred to the measurement chamber from the reference chamber, and wherein the measurement chamber end of the capillary tube is disposed in close spatial relationship to the plating surface of the test electrode;

selectively controllable electroplate driving electronics electrically and operatively coupled between the test electrode and the electroplating current source electrode, whereby metal is selectively deposited onto the test electrode from the mixed metal plating solution in the mixing chamber at a constant or known current density; and electrical potential measuring circuitry electrically and operatively coupled between the test electrode and the reference electrode, whereby electrical potential between the electrodes is measured and recorded.

2. The metal plating bath analysis apparatus of claim 1, wherein the test electrode is selected from the group consisting of rotating disc electrodes and ultra-micro electrodes.

3. The metal plating bath analysis apparatus of claim 1, wherein the test electrode is operatively coupled to a hydrodynamic actuator, such that a reproducible flow of mixed base metal plating solution in the measurement chamber is directed against an operative surface of said test electrode.

4. The metal plating bath analysis apparatus of claim 3, wherein the hydrodynamic actuator is selected from the group consisting of ultrasonic vibrators, mechanical vibrators, propellers, pressure differential fluid pumps, static mixers, gas spargers, magnetic stirrers, fluid ejectors, and fluid eductors.

5. The metal plating bath analysis apparatus of claim 1, wherein the test electrode is disposed within the measuring chamber at an acute angle between 3 and 45 degrees from vertical.

6. The metal plating bath analysis apparatus of claim 1, wherein the test electrode comprises a material selected from the group consisting of noble metals and glassy carbon.

7. The metal plating bath analysis apparatus of claim 6, wherein the noble metals comprise metals selected from the group consisting of platinum and gold.

* * * * *